United States Patent [19]

Hasson

[11] Patent Number: 4,760,848
[45] Date of Patent: Aug. 2, 1988

[54] ROTATIONAL SURGICAL INSTRUMENT

[76] Inventor: Harrith M. Hasson, P.O. Box 14898, Chicago, Ill. 60614

[21] Appl. No.: 925,900

[22] Filed: Nov. 3, 1986

[51] Int. Cl.[4] .................. A61B 17/00; A47F 13/06; B25B 1/00

[52] U.S. Cl. .................................. 128/340; 294/19.1; 294/115; 128/321

[58] Field of Search ............... 128/346, 321, 303 R, 128/334 R, 340, 19.1, 115; 294/19.1, 22, 15; 81/302, 57.43

[56] References Cited

U.S. PATENT DOCUMENTS

| | | | |
|---|---|---|---|
| 268,153 | 11/1882 | Turner | 294/115 |
| 273,243 | 3/1883 | Adams | 294/115 |
| 1,758,364 | 5/1930 | Jesen | 294/115 |
| 2,790,437 | 4/1957 | Moore | 294/19.1 |
| 3,094,349 | 6/1963 | Schwalm | 294/115 |
| 3,506,012 | 4/1970 | Brown | 128/346 |
| 4,039,216 | 8/1977 | Soos | 294/19.1 |
| 4,575,143 | 3/1986 | Nast | 294/19.1 |

FOREIGN PATENT DOCUMENTS 771120  10/1934  France ................ 294/19.1

Primary Examiner—Richard C. Pinkham
Assistant Examiner—Gary Jackson
Attorney, Agent, or Firm—Wood, Dalton, Phillips, Mason & Rowe

[57] ABSTRACT

An instrument according to the present invention comprises a casing, an exposed working head with an associated movable element, an actuating link slidably mounted relative to the casing for moving the element and an actuator mechanism with a control portion for sliding the actuating link. The actuating link is biased slidably in a first direction relative to the casing which urges the jaws, blades, etc. to a closed position. Upon radially depressing the control portion, the actuator mechanism causes the actuating link to move against the spring bias slidably in a direction opposite to the first direction. Structure is provided to selectively lock the jaws on the working head in an open position. Successive depressions of the control portion of the actuator mechanism alternatingly lock the jaws open and closed. Because the jaws are urged to a closed position, the user does not have to maintain constant closing pressure during use yet the user has the ability to easily lock the jaws in an open position.

15 Claims, 2 Drawing Sheets

U.S. Patent  Aug. 2, 1988  Sheet 1 of 2  4,760,848
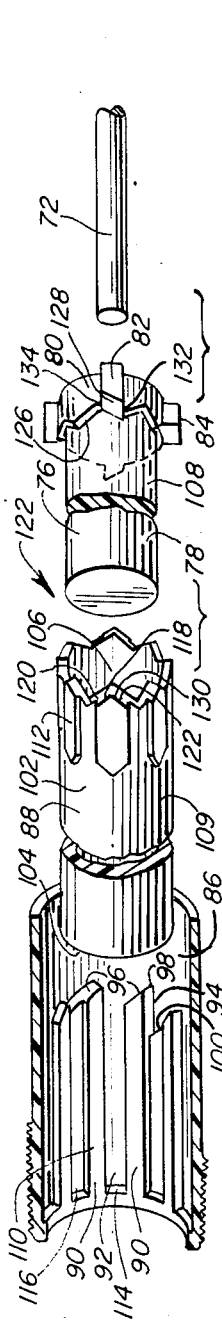
FIG. 2
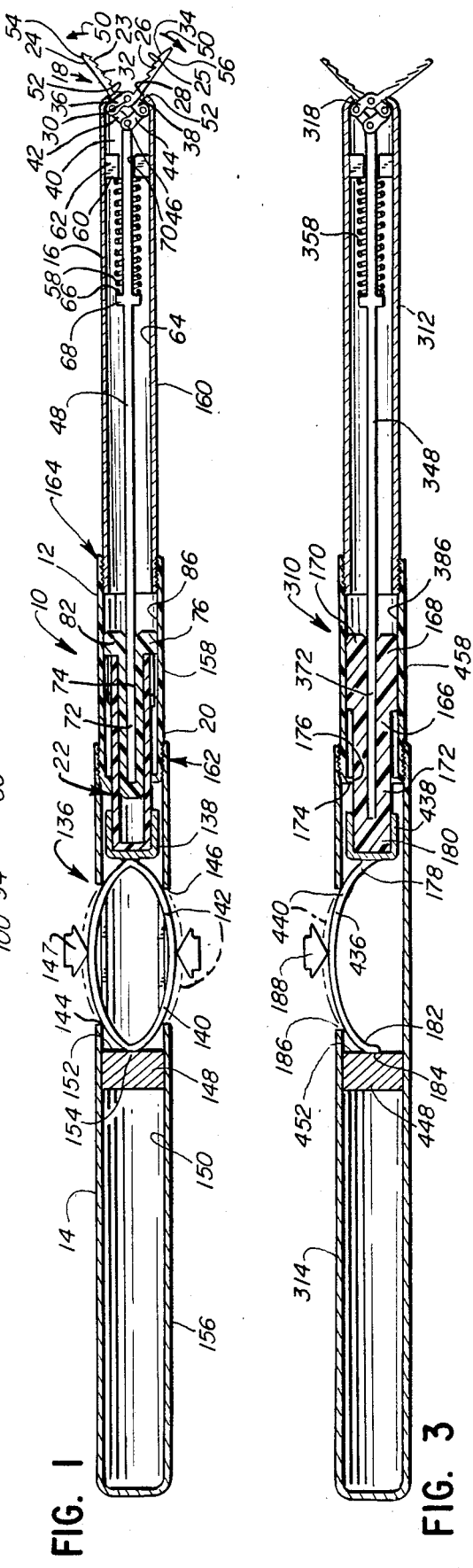
FIG. 1
FIG. 3
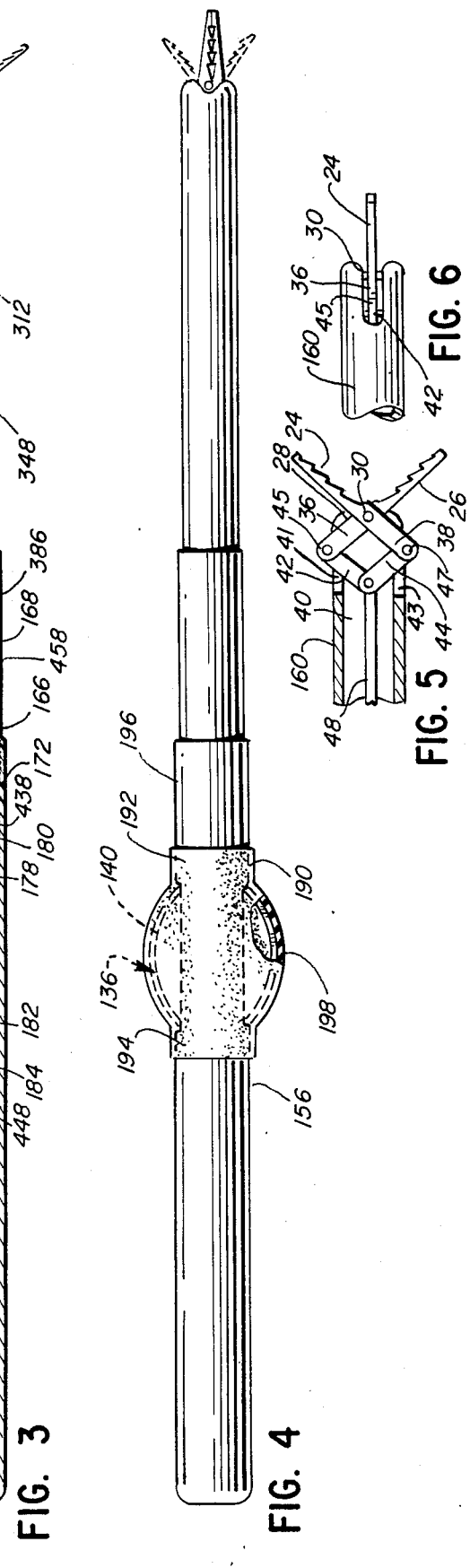
FIG. 4
FIG. 5
FIG. 6

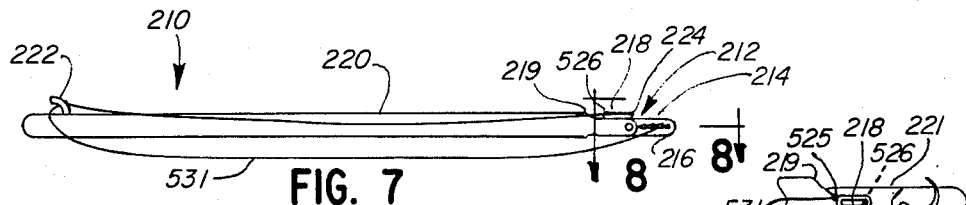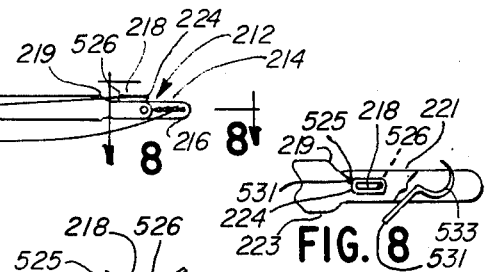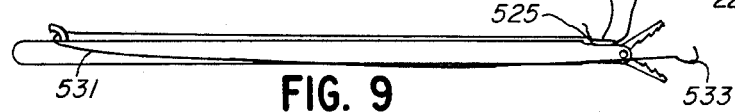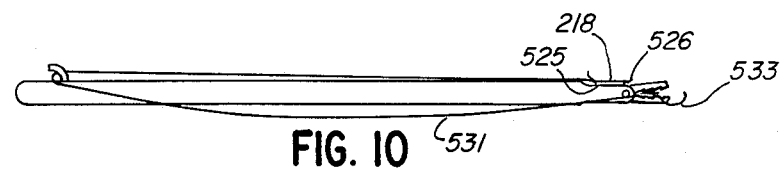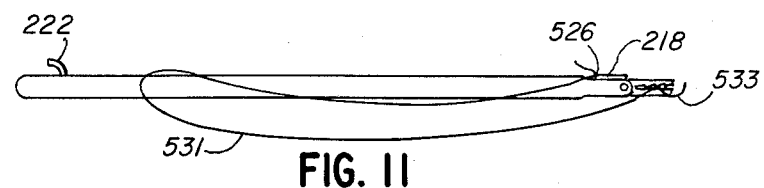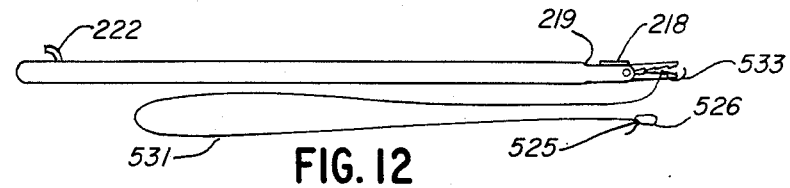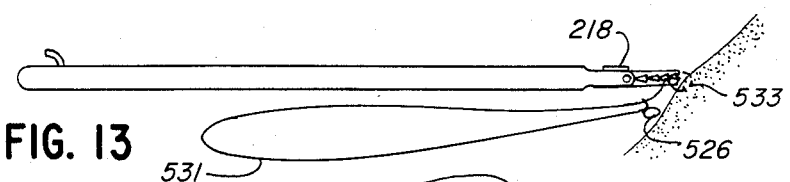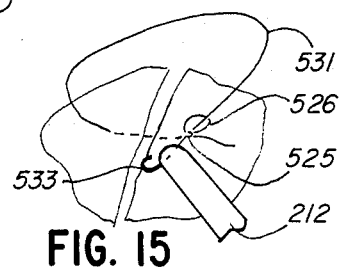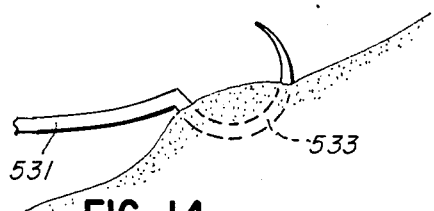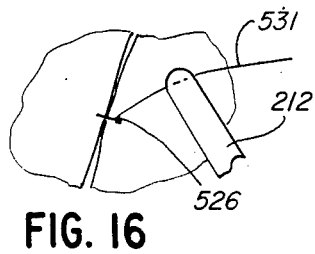

ROTATIONAL SURGICAL INSTRUMENT

BACKGROUND OF THE INVENTION

1. Field of the Invention

This invention relates to surgical instruments having a working head with an associated movable element that is controllable from a location remote from the working head.

2. Background Art

Delicate surgical operations such as microsurgery and laparoscopy surgery often require precise control over jaws or blades of instruments used in the procedure. In order to achieve maximum control over these instruments, it is necessary to use the intrinsic muscles of the hand which are capable of considerable control and remarkable finesse. It is known that muscles that control motion of the fingers are capable physiologically of more precise motion than muscles that control flexion, extension or rotation of the wrist or those muscles that control supination/pronation of the forearm. The motor and sensory innervations of the hand are significantly out of proportion to the size or bulk of the hand.

Heretofore, surgical instruments have not been designed to exploit the hand muscles that give maximum dexterity. For example, one type of instrument has a scissors-type grip which is operated to slide a cable or actuating link within a flexible casing to selectively open and close cooperating jaws, blades or the like. To effect rotation of the jaws the entire instrument must be rotated through the grip primarily with the wrist which, as previously described, gives the user a limited amount of control.

If the casing is not maintained perfectly straight, part of the instrument will not rotate about the axis of the casing. Substantial tissue damage may then occur. Additionally, the working head might nutate upon rotation of the instrument. This cannot be tolerated in delicate surgical procedures.

Another problem with the aforementioned structure is that the user must constantly maintain pressure on the grip to close the jaws or the blades. It is awkward and inconvenient to squeeze the grip as the instrument is being used during an operation and muscular fatigue is inevitable.

Another problem in gynecological microsurgery that has been inadequately dealt with by the prior art is that of tying delicate sutures in areas which are not readily accessible. Procedures now used generally inordinately lengthen operative time. There is also a tendency of sutures formed by conventional techniques to loosen and release altogether.

SUMMARY OF THE INVENTION

It is the principal objective of the present invention to provide surgical instruments of a novel design and construction that can be easily held in the hand and operated by its intrinsic muscles. Proper use of intrinsic muscles of the hand for delicate surgery can be achieved in two ways: (1) by placing the operating instrument between the thumb, index and middle fingers in the familiar three finger pencil grip with the instrument handle resting in the first web space; or (2) by placing the instrument between the thumb, index and middle fingers with the handle of the instrument resting inside the palm. To facilitate holding of instruments comfortable in either position for long periods of time without fatigue or tremors, instruments according to the present invention are made generally cylindrical. A cylindrical form similar to that of a cylindrical ball point pen or pencil also facilitates rotation of the instruments for manipulation. This is accomplished as the thumb rolls the instrument, like a pencil, on the index and/or middle finger while the instrument is supported and counter balanced in the first web space, with the instrument held in the first position, or by a portion of the small and/or ring finger counter balancing the instrument against the palm of the hand, with the instrument held in the second position.

The rotational technique has several advantages: (1) it allows the hand to remain relaxed during the procedure, thereby suppressing tremors and tension; (2) it produces a spindle-like motion that is smooth and precise and highly controllable; (3) it permits manipulation of the instrument smoothly through its natural arc of rotation rather than moving the whole hand, including the instrument through the much larger rotational arc of the pronating-supinating forearm; and (4) it provides greater vision of the operative field as the instrument can be easily moved out of the line of sight by a slight change in the holding angle. The rotational technique minimizes tissue damage. For instance, the needle in the case of a needle holder is spun gently through the tissue rather than pushed coarsely into it.

Instruments according to the present invention typically have an exposed working head having at least one associated movable element such as a jaw or blade having open and closed positions. The jaws or blades may be in the form of needle holder, scissors, tissue forceps, smooth holding platform or other forceps. These surgical instruments, when configured as the present invention contemplates, are held comfortably between the thumb, index and middle fingers, resting either in the first web space or inside the palm. These novel instruments are easily rotated between the thumb and index and/or middle finger counter balanced either by the muscles of the first web space or by the muscles of the palm.

More specifically, an instrument according to the present invention comprises a casing, an exposed working head with an associated movable element, an actuating link slidably mounted relative to the casing for moving the element and an actuator mechanism with a control portion for sliding the actuating link.

The actuating link is biased slidably in a first direction relative to the casing which urges the jaws, blades, etc. to a closed position. Upon radially depressing the control portion, the actuator mechanism causes the actuating link to move against the spring bias slidably in a direction opposite to the first direction. Structure is provided to selectively lock the jaws, blades, etc. on the working head in an open position. Successive depressions of the control portion of the actuator mechanism alternatingly lock the jaws open and closed. Because the jaws are urged to a closed position, the user does not have to maintain constant closing pressure yet the user can still easily lock the jaws open.

In one form of the invention, the casing has an opening to admit the control portion of the actuator mechanism. To adapt the instrument for laparoscopic and pelviscopic surgery, a resilient element is disposed sealingly over the opening to permit operation of the control portion of the actuator mechanism and at the same time prevent passage of gas through the opening i.e. the escape of gas out of the abdomen during the performance of an operation.

The invention further contemplates the provision of a structure and a process for facilitating internal suturing, as for example inside the abdomen during laparoscopy surgery. According to the invention a noose or sliding knot is preformed in thread used to make the suture. A structure is provided to controllably insert the noose and a needle into the abdomen. The needle can then be directed through the tissue and noose loop and pulled to create a knot as the tightened noose firmly captures the suture. The first knot 50 readily formed serves as a firm anchor, which feature is particularly desirable in the case of microsurgical or laparoscopic procedures.

BRIEF DESCRIPTION OF THE DRAWINGS

FIG. 1 is a sectional view of a surgical instrument according to the present invention;

FIG. 2 is an enlarged, exploded perspective view of an actuator mechanism associated with the instrument in FIG. 1;

FIG. 3 is a sectional view of a modified form of surgical instrument according to the invention;

FIG. 4 is a side elevation view of the instrument in FIG. 1 and modified by the inclusion of a sealing member over an opening in the instrument casing;

FIG. 5 is an elevational view of another form of end portion for the surgical instrument of FIGS. 1–4;

FIG. 6 is a top view of the form of instrument shown in FIG. 5.

FIG. 7 is the instrument of FIG. 1 being used as a suturing instrument;

FIG. 8 is an enlarged, partial sectional view taken along the section 8—8 of FIG. 7; and FIGS. 9–16 are the instrument of FIG. 8 used as a suturing instrument to perform the various steps sequentially in the process of knotting the suture.

DETAILED DESCRIPTION OF THE DRAWINGS

Referring initially to FIG. 1, a surgical instrument according to the present invention is shown generally at 10. The instrument 10 comprises a three-part cylindrical casing 12 with a handle section 14, a working end portion 16 having an associated working head 18, and a control section 20 with an associated actuator mechanism at 22. The casing as shown is of metal, but could be of other appropriate materials and is generally on the order of 5–15 mm in outside diameter.

The inventive structure is described herein as including a working head 18 comprising a pair of jaws 24, 26 that are selectively movable towards and away from each other. It should be understood that the invention does not contemplate any specific configuration for the working head. For example, blades might be substituted for the jaws and the working head might take the form of a needle holder, scissors, tissue forceps, smooth holding platform, etc.

The operation of the jawed working head 18 will now be briefly described. The distal end of the working portion 16 of the casing 12 has a slotted opening 28 through which the jaws 24, 26 extend. The jaws 24, 26 are connected at intermediate points for pivoting movement about a pin 30 which is attached to the casing adjacent to the opening 28 so that the free ends 32, 34 of the jaws 24, 26 are exposed at the distal end of the casing. The cooperating surfaces 23, 25 of the jaws 24, 26 may have a saw tooth configuration to enhance the gripping capacity of the working head or they may consist of sharp blades or be smooth as described above. The proximal ends 36, 38 of the jaws 24, 26 reside within a hollow portion 40 of the casing and are respectively pivoted to links 42, 44, which are in turn commonly connected for pivoting movement about pin 46. An actuating link 48 is also pivotally connected to pin 46 and upon forward movement (to the right in FIG. 1) relative to the casing drives the jaws 24, 26 through links 42, 44 in the direction of arrows 50 to an open position. Retraction of the actuating link 48 (i.e. movement to the left in FIG. 1) draws on the links 42, 44 to close the jaws against each other. The opening 28 is bounded by abutting surfaces 52 which each make less than a 90° angle with the axis of the casing and abut jaw surfaces 54, 56 to limit the extent of opening of the jaws.

FIGS. 5 and 6 show another form of instrument wherein the tip portion is provided with aligned slots 41 and 43 in the upper and lower surfaces of the casing. The slots 41 and 43 align with the slotted opening 28. The pivots 45, 47 between the jaws 24, 26 and links 42, 44 extend outwardly through the slots 41, 43 when the jaws 24, 26 are open and retract into the casing when the jaws are closed.

The actuating link 48 is guided slidingly within the hollow portion 40 of the casing between the jaw open and jaw closed positions. The actuator link 48 is biased rearwardly (to the left in FIG. 1) by a compressed coil spring 58 which surrounds the actuating link 48 and is captively maintained between the rearwardly facing surface 60 of a restraint 62 mounted to the inside surface 64 of the working end of the casing and the forwardly facing surface 66 of a radial enlargement 68 on the actuating link 48. There is a constant pressure exerted on the actuating link by the spring 58 tending to close the jaws. The closing force of the jaw is thereby a function of the spring constant.

The link is guided at its distal end by an annular surface 70 in the restraint 62 which surface 70 bounds an axial passageway for the actuating link. The proximal end 72 of the actuating link 48 is accepted in a bore 74 within a first actuator control element 76. The control element 76, as seen clearly in FIG. 2, comprises a cylindrical body 78 with an enlarged head 80 having two pairs of diametrically opposite, radial projections 82, with surfaces 84 thereon that move guidingly against the inside surface 86 at the central portion of the casing 12.

The actuating link 48 is controlled by the actuator mechanism 22, which is shown clearly in FIGS. 1 and 2. The actuator mechanism 22 comprises the aforementioned first control element 76 and a second actuator control element 88 which cooperate with each other and the inside surface 86 of the casing in effecting controlled movement of the actuating link 48. A plurality of axially aligned ribs 90 are spaced equidistantly about the inside surface 86 and project radially inwardly therefrom. Four long slots 92 and four short guide slots 94 are formed alternatingly between adjacent ribs 90. Each rib 90 has an angled, forward ramp surface 96 with a forward apex 98. The short guide slots are bounded axially by surfaces 100, which are inclined in the same direction as the ramp surfaces 96.

The second control element 88 has a cylindrical body 102 with a closed end 104 and an open end having an inside, cylindrical surface 106 which is of slightly larger diameter than the outer surface 108 of the cylindrical body 78 of the first control element 76 so that the control elements can be nested, one within the other. The outer surface 109 of the body 102 has a diameter slightly less than the diameter defined cooperatively by the radially inwardly facing surfaces 110 on the ribs 90 and is guided thereby as described below.

Projecting radially outwardly from the outer surface 109 of the control element 88 are a plurality of guiding ribs 112. The guiding ribs are of a width to fit in both the long and short slots 92, 94 between ribs 90, guide relative axial movement between the casing and second control element 88 and abut shoulders 114 at the bottom of the slots to limit rearward shifting of the control element 88 relative to the casing. To prevent interference between the ribs 112 and surfaces 100 at the bottom of the short slots 94, the surfaces 116 between ribs 90 and behind the pass the ribs so that the ribs can move fully back into abutting relationship with the shoulders 114 bounding the short slots as well as the long slots.

The forward edge 118 of each rib 112 is defined by two angled surfaces 120, 122 cooperatively defining a rearwardly opening V with a centerline aligned with the axis of the body 102. The surfaces 120, 122 on all the ribs define a regular, saw tooth arrangement about the forward edge 118 of the control element 88. With the body 78 of the first control element 76 nested within the second element 88, a rearwardly facing edge 126 on the element 76, with a configuration complementary to the edge 118, engages the edge 118 to prevent relative rotation between the first and second control elements 76, 88.

Each of the projections 82 on the first control element 76 is dimensioned to move guidingly within the slots 92, 94 and alternatively all projections 82 are in short slots 94 or long slots 92. Each projection 82 has a rearwardly facing, inclined surface 128. With the first control element 76 nested in the second control element 88, and the ribs 112 and projections 82 within the guide slots 92, 94, each apex 130 between the surfaces 120, 122 rests on the surface 128 midway between spaced ends 132, 134 thereon. Upon the first and second control elements being urged axially towards each other, there is a tendency of the apex 130 to ride forwardly up the inclined surface so that the control elements tend to turn against each other. This relative turning is resisted by the ribs 90.

In operation, the actuator mechanism works as follows. The spring 58 normally biases the first control element 76 into nested relationship with the second control element and in turn the second control element 88 rearwardly. In a jaws closed position, the guiding ribs 112 move rearwardly into abutting engagement with the shoulders 114 on the casing. In this position, the projections 82 on the first control element reside within the long slots 92. Upon the second actuator element being moved forwardly, the ends 132 of the surfaces 128 will move out of the slots axially forwardly beyond the apexes of the ribs 90, whereupon the apexes 130 will slide rotatively further towards the ends 134 of the surfaces 128 so that an increment of rotation is imparted to the first control element. Upon releasing the second control element, the apexes 98 of the ribs will align with the surfaces 128 between the ends thereof and, upon the first control element 76 being urged rearwardly by the spring 58, cause a second increment of rotation of the first control element to occur. The surfaces 96 on the ribs 90 and the surfaces 128 on the projections 112 then cooperate to guide the projections into alignment with the short slots 94. The spring 58 urges the surfaces 100 bounding the short slot facially against the surfaces 128 on the projections. The actuating link is thereby keyed against rotation by the cooperation of the projections 112 and the ribs 90 and surface 100 and the jaws are locked in an open position.

It can be seen that upon shifting the second actuator element a predetermined amount axially and thereby releasing it that the control element 76 will be incrementally rotated. The jaws will alternatingly be positioned lockingly in a closed and open position upon the second actuator element being successively operated. Each operation of the actuating element produces the same increment of rotation.

To effect axial shifting of the control elements, a control portion at 136 is provided on the actuator mechanism 22. The control portion 136 comprises a cylindrical, forwardly opening cap 138, which surrounds the closed end 104 of the second actuating element. Integrally formed with the cap 138 is a spring element 140 defining a closed loop 142 made of stiff, resilient material with good memory. To accommodate the loop 142, the handle section 14 of the casing has radially opposite openings 144, 146 through which portions of the loop radially project. A blocking element 148 is fixed to an inside, cylindrical surface 150 on the handle section 14 and has a forwardly facing shoulder 152 for abutment with the rearwardmost edge 154 of the loop 142.

With the jaws in a closed position, the spring 58 urges the actuating link and first and second control elements rearwardly so that the loop 142 is compressed against the shoulder 152 on the blocking element 148. This distorts the loop radially outwardly to the position shown in phantom in FIG. 1. By pressing diametrically opposite edges of the loop radially inwardly in the direction of arrows 147, the cap is urged axially forwardly of the casing to effect opening of the jaws.

With this arrangement, one can grasp the handle portion of the casing so that the loop is situated conveniently between the thumb and index finger. Upon compressing the loop between the thumb and index finger, the loop is flattened to thereby urge the jaws forwardly to their open position.

The casing 12 in FIG. 1 is shown to comprise three cylindrical sections—a handle section 156, a central section 158 and a forward section 160. The handle section 156 and central section 158 are threadably mated, one within the other at 162. The central section and forward section are also threadably mated, one within the other at 164. The multi-part casing is an optional feature that is desirable as it facilitates assembly and cleaning of the instrument.

An alternative type of surgical instrument according to the invention is shown at 310 in FIG. 3. The structure is different from that in FIG. 1 principally in two respects. First, the actuator mechanism 166 will only cause axial shifting of the actuator link 348 but will not selectively lock the jaws in an open position.

The instrument 310 has a hollow casing 312 within which the actuator link 348 is slidingly guided. The actuator mechanism 166 comprises a cylindrical slide 168 within which the proximal end 372 of the actuator 348 is imbedded. The slide has a stepped configuration with a large diameter portion 170 and a small diameter portion 172. The large diameter portion is closely guided for axial movement against the inside surface 386 of the central section 458. The rearwardmost edge of the central section is inturned to define an annular flange 174. The flange 174 has an opening with a bounding surface 176 to closely, guidingly accept the small diameter portion 172.

A further difference between the structure in FIG. 3 and that in FIG. 1 is in the spring element 440. Whereas the spring element 140 in the FIG. 1 embodiment comprises a closed loop, the spring element 440 in FIG. 3 comprises a gently curved, U-shaped element. One leg 178 of the U is integrally formed with the cap 438 surrounding the free end 180 of the small diameter portion 172. The other leg 182 has a free end 184 that is offset and which bears against the forwardly facing shoulder 452 on the blocking element 448. The casing has a single opening 186 through which the spring element radially projects.

The slide 168 and actuating link 348 are shifted axially forwardly upon the spring element 440 being depressed from the phantom position in FIG. 3 in the direction of arrow 188 to the flattened solid line position. To accomplish this, the handle section 314 is grasped by the user so that the thumb is located adjacent to the radially projecting spring element 440. Upon being radially depressed, the spring element 440 is effectively lengthened and the jaws thereby opened against the bias of spring 358.

It is important in laparoscopic and pelviscopic surgery that abdominal gases be confined. One potential problem with this type of operation using the structure in FIGS. 1-3 is that the gases may escape through the openings 144, 146 and 186 through which the spring elements 140, 440 associated with the control portions 136, 436 extend. To overcome this problem, a resilient boot 190, such as shown in FIG. 4, is disposed sealingly over the openings. The boot 190 comprises spaced, cylindrical sections 192, 194, which closely, sealingly surround the outer surface 196 of the handle section 156 of the casing. The central portion 198 of the boot conforms to and surrounds the projecting control portion 136 and is compressible radially upon the spring element 140 being moved radially to operate the jaws.

Another aspect of the invention is the provision of a structure to facilitate suturing and a process for suturing using the inventive structure. The inventive structure is shown in FIGS. 7-16 and the steps to be performed to make a suture are shown sequentially in those same figures.

A surgical instrument shown generally at 210 in FIGS. 7-16 is modified according to the invention. The basic instrument 210, in this case a needle holder, comprises generally a working head 212 with movable jaws 214, 216, selectively controllable by an actuator of the type shown in FIGS. 1-4 and previously described herein.

The instrument 210 is modified by providing a flexible bracket 218 (FIGS. 7 and 8) on the instrument body 220 adjacent to the working head 212 and a second bracket 222 on the body 220 in spaced relationship with the bracket 218 and remote from the working head 212. The bracket 218 is located forward of a shoulder 219 in a distal portion 221 having a reduced diameter as compared to the body 220 of the instrument. The amount of reduction in the diameter is sufficient to position the outermost edge of the bracket 218 within the confines of the outer diameter of the body 220. In other words, the bracket 218 projects radially outward less than the outer surface of the body 220 so that the bracket will not hang up when the instrument is removed from a trocar tube. Each of the brackets 218, 222 projects from the body 220 and is slightly curved to define a U in conjunction with the body opening away from the working head 212. The bracket 218 has a notch 224 to receive, seat and retain the end of a thread as thereafter described. Before this structure and its advantages can be fully understood, the basic suturing procedure should be explained.

To facilitate suturing inside the abdomen during laparascopy surgery, the invention contemplates forming a noose loop (sliding knot or hangman's noose) and holding and stabilizing the loop on a needle holder prior to suturing. There are certain advantages to making a knot by passing the needle of a suture through a loop previously formed therein as will be enumerated below.

The pre-formed loop needs to have a sliding knot and to be located near the distal end of the suture. Ideally, sutures with pre-formed distal noose loops possessing optimum features including loop size and length of short end, would be prepared and packaged ready for use by the manufacturer. However, the surgeon and/or scrub nurse can easily prepare a number of these sutures before and during the operation.

There are several ways to form a noose defined as a loop with a sliding knot. A portion of the suture near the distal or free end is crossed so as to form a loop and the crossing point is held between the thumb and index fingers. A needle holder is introduced into the loop, in the closed position, and turned in a circular fashion so as to form a FIG. 8 twist within the loop. A more proximal portion of the suture is then grasped, held with the instrument and pulled through the loop against the distal end of the suture being held between the thumb and index fingers. The noose forms and its running knot tightens with continued pulling of one suture point of fixation against the other. Initially, the loop of the noose binds closer as it is drawn, eventually, continued pulling will cause the knot to unravel. However, if the needle of the suture is passed through the noose loop before it unravels, a stable knot is formed at the end of the pull.

Another way of forming a noose will now be briefly described. The suture is held in the left hand between the thumb and index fingers and looped around the hand, or a portion thereof, over the thumb, between the index and middle fingers. The right hand holds the distal end of the suture which was being held between the thumb and index fingers of the left hand, as the index and middle fingers of the left hand pull the suture held between them, inside the previously-formed loop, to form the noose. Once the noose knot is tightened, the noose loop made reasonably small and the free end of the suture trimmed short, the suture is ready for use.

It should be noted that the inventive technique requires the use of a tissue forceps or needle holder with delicate or plain jaws, to prevent fraying of the suture, and that the two instruments can often be used interchangeably. In a typical application, the needle of a suture containing a distal noose is passed through two opposing tissue surfaces and pulled out as usual. With continued pulling, the knot 525 of the noose 526 comes to rest against the opposite tissue surface (FIG. 15), being too bulky to slip through, and binds closer as it is drawn. The next step is to pass the needle 533 through the noose loop (FIG. 15), and then to pull the suture firmly into a knot. If interrupted sutures are used, at least one more tie is required to lock the knot in place. However, with contiuous sutures, the needle through the loop knot can stand alone, as it would be impossible for the knot to slip or loosen under such circumstances.

In order not to lose needles into the abdomen it is recommended that the sutures and needles used in laparascopy surgery not be any smaller than 5-0 size.

Advantages of this technique include:

1. Inadvertent slippage of the free short end of the suture into and/or out of the tissues is minimized: the noose knot generally offers sufficient resistance to prevent such an occurrence.

2. The first and usually most difficult knot is made with greater accuracy and ease.

3. In the case of interrupted sutures, a second tie is made over a tightened stable knot rather than over a first tie which may loosen and become ineffectual between throws. A greater amount of time is saved with continuous sutures as the needle through the noose technique is all that is required for a secure knot.

The formation of suture loops on the basis of turning the suture clockwise and counterclockwise presents an opportunity for making square knots consistently, with the use of instruments. The method appears to be easily reproducible and particularly helpful in less accessible areas.

A portion of the suture located within the operative field is held with a needle holder and turned to form a loop. The crossing point of the loop is held and stabilized with a forceps manipulated with the other hand, and the stable loop is brought into the vicinity of the free or distal end of the suture. The needle holder is placed under the curve of the stable loop and advanced so as to catch and hold the short end of the suture inside the loop. The forceps which has been stabilizing the loop is now repositioned onto the proximal or needle side of the suture and both sides are pulled against each other to form a tie.

The procedure is reversed in order to make a square knot. The suture is held with the needle holder and turned counterclockwise to form a loop. Again, the crossing point of the loop is held and stabilized with a forceps and the stable loop is moved close to the distal end of the suture. The needle holder is then placed over the curve of the stable loop so as to catch and hold the distal end of the suture inside the loop. The forceps is repositioned to hold the needle side of the suture and the two points of suture fixation are pulled against each other to form the tie required for a square knot. Another tie of either type is usually added for greater security of the knot.

The above procedure will now be described in detail with reference specifically to FIGS. 7-16. A noose loop 526 is preformed, as described above, at the distal end of a suture 531 and the loop is placed in the notch 224 on the loop bracket 218 as shown in FIGS. 7 and 8. The suture is then guided backward (proximally) over and around the bracket 222 and then forward distally where a needle 533 is grasped and stored within the jaws 214, 216 of the needle holder as shown in FIG. 7. FIG. 8 shows one jaw broken away with the needle in position on the other jaw. This is the initial position of the needle of FIG. 7 ready for insertion through an introducer tube. After the needle holder is introduced into the abdomen with the needle and thread for the purpose of suturing inside the abdomen during laparascopy, the needle is released, as shown in FIG. 9 by opening the jaws of the needle holder and then the suspended needle is grasped in good orientation for suturing as in FIG. 10. A second instrument (not shown) is utilized during this step. The suture is then gently disengaged first from bracket anchor 222 and then bracket 218, as shown in FIGS. 11-13, thereby releasing the intact noose loop into the abdomen. Following passage of the needle in opposing tissue surfaces as shown in FIGS. 13 and 14, the suture is pulled until the knot 525 of the noose contacts the skin where the suture needle had initially entered. The distal end does not slip because of the presence of the noose loop. The needle is then passed through the noose 526 as shown in FIG. 15 and pulled, creating a knot as shown in FIG. 16. A second throw is then added to stabilize the knot and secure it, as needed.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. An improved instrument of the type having a longitudinal casing, an exposed working head with an associated element that is moveable between an open position and a closed position, an actuating link slidably mounted relative to the longitudinal casing for moving said element selectively between said open and closed positions, and an actuator mechanism for sliding said actuating link, the improvement comprising:
   means biasing the actuating link so that the working head element is urged towards said closed position,
   said actuator mechanism including means responsive to a laterally directed force to move the actuating link against a force exerted by the biasing means to move the working head element toward said open position.

2. The improved instrument according to claim 1 wherein means are provided to lock the working head element in said open position.

3. The improved instrument according to claim 1 wherein said casing has a cylindrical portion defining a handle for holding the instrument and said actuator mechanism has a control portion projecting radially through the cylindrical casing portion for operating the actuator mechanism.

4. The improved instrument according to claim 1 wherein said casing has a cylindrical portion with an opening therein, said actuator mechanism has a control portion projecting radially through the opening for operating the actuator mechanism upon said control portion being moved laterally in relation to the casing and a resilient member is disposed sealingly over the casing opening.

5. The improved instrument according to claim 1 wherein said actuator mechanism has a portion that is rotated incrementally upon the actuator mechanism being operated and in a first rotational position of said actuator mechanism portion said working head element is locked in said open position and in a second rotational position of said actuator mechanism portion the biasing means urge the working head element towards its closed position.

6. The improved instrument according to claim 1 wherein said casing has a cylindrical portion, said cylindrical casing portion has axially spaced ends and said actuator mechanism has a control portion that projects radially from the casing between the axially spaced ends thereof.

7. An improved surgical instrument of the type having a casing, an exposed working element having the type having a casing, an exposed working element having at least one pivotable jaw, an actuating link slidably mounted relative to the casing for pivoting said jaw, and an actuator mechanism for sliding said actuating link, the improvement comprising:

means for biasing the actuating link slidably in a first direction so that the jaw is biased towards a closed position;

said actuator mechanism including means responsive to a laterally directed force to move the actuating link against a force exerted by the biasing means in a second direction opposite to the first direction and for moving the jaw to an open position; and means for selectively locking the jaw in an open position.

8. The improved surgical instrument according to claim 7 wherein said actuator structure has a portion that is movable relative to the casing and said actuator structure portion and casing have cooperating means to maintain the jaw in the open position.

9. The improved surgical instrument according to claim 7 wherein said casing has a cylindrical configuration with an open end, the jaw is adjacent said open end, means mount the actuating link for guided sliding movement within the casing and said actuator mechanism has a control portion that is movable laterally inwardly in relation to the casing to cause said actuating link to move in said second direction.

10. The improved surgical instrument according to claim 7 wherein said casing has a cylindrical portion, the actuator mechanism has a portion that is rotatable about the casing axis between a first position wherein the actuator mechanism portion cooperates with the housing to maintain the jaw in an open position and a second position wherein the biasing means causes the jaw to be urged towards its closed position and means are provided to incrementally rotate the actuator mechanism portion between the first and second positions of the actuator mechanism portion.

11. The improved surgical instrument according to claim 9 wherein the control portion comprises a spring element that is deflectable radially of the casing to effect movement of the actuating link.

12. The improved surgical instrument according to claim 9 wherein said casing has axially spaced ends and the control portion resides axially between the spaced casing ends so that the casing can be grasped adjacent one end for facilitated operation of the control portion.

13. An improved instrument of the type having a casing, an exposed working head with an associated movable element that is movable between an open position and a closed position, an actuating link slidably mounted relative to the casing for moving said element and an actuator mechanism for sliding said actuating link, the improvement comprising:

said casing having a cylindrical portion defining a handle for holding the instrument; and said actuator mechanism having a control portion responsive to a laterally directed force to move the actuating link and the associated movable element, whereby a user can grasp the cylindrical casing portion and move the control portion with one hand to operate the movable element.

14. The improved instrument according to claim 13 wherein said cylindrical portion has an opening and the control portion projects through said opening.

15. The improved instrument according to claim 13 wherein said movable element has a closed position and an open position and means bias the movable element towards the closed position for the movable element.

* * * * *